US00PP13178P2

(12) United States Plant Patent
Doguet

(10) Patent No.: US PP13,178 P2
(45) Date of Patent: Nov. 5, 2002

(54) ZOYSIAGRASS PLANT NAMED 'JAMUR'

(75) Inventor: David Doguet, Austin, TX (US)

(73) Assignee: Bladerunner Farms, Poteet, TX (US)

( * ) Notice: Subject to any disclaimer, the term of this patent is extended or adjusted under 35 U.S.C. 154(b) by 0 days.

(21) Appl. No.: 09/059,591

(22) Filed: Apr. 14, 1998

(51) Int. Cl.[7] ..... A01H 5/00
(52) U.S. Cl. ..... Plt./390
(58) Field of Search ..... Plt./390, 388

(56) References Cited

U.S. PATENT DOCUMENTS

PP6,516 P * 1/1989 Whiting ..... Plt./390
PP11,004 P 7/1999 Doguet
PP11,515 P 9/2000 Engelke
PP11,570 P 10/2000 Engelke

* cited by examiner

*Primary Examiner*—Bruce R. Campell
*Assistant Examiner*—W C Baker
(74) *Attorney, Agent, or Firm*—Streets & Steele; Jeffrey L. Streets

(57) ABSTRACT

This newly discovered asexually reproduced variety of zoysiagrass plant is a perennial, having a superior rate of spreading with texture improved over common zoysiagrass, superior turf grass quality regarding compactness and low degree of thatch, and slightly darker than average green color.

3 Drawing Sheets

BACKGROUND OF THE INVENTION

The present invention relates to a new and distinct variety of a Zoysiagrass plant. The plant is a progeny that was discovered by David Doguet of Poteet, Tex., of a zoysiagrass plant in a collection of plants from Kobe, Japan made by Jack Murray (deceased). From these progenies, as seeds, were grown a collection of plants from which David Doguet discovered the single plant that was later cloned into sod and call 'JaMur'.

For purposes of registration under the "International Convention for the Protection of New Varieties of Plants" (generally known by its French acronym as the UPOV Convention) and noting Section 1612 of the Manual of Patent Examination Procedures the new variety of zoysia grass of the present invention is named 'JaMur'.

BRIEF SUMMARY OF THE INVENTION

The plant dimensions of 'JaMur' are intermediate between the large dimensions of 'Chinese Common' (unpatented) and 'El Toro' (U.S. Plant Pat. No. 5,845) and the smaller dimensions of 'Meyer' (unpatented) and 'Emerald' (unpatented). The wide leaf blades of 'JaMur' give it a coarse texture comparable to that of 'Chinese Common' or 'El Toro', but its short stature in sheath and blade length and less vertical posture result in a more compact turf. The compactness of 'JaMur', coupled with its superior rate of spread and low degree of thatch, make 'JaMur' a novel and improved addition to available zoysiagrass turfs.

DETAILED BOTANICAL DESCRIPTION

Figure 1:
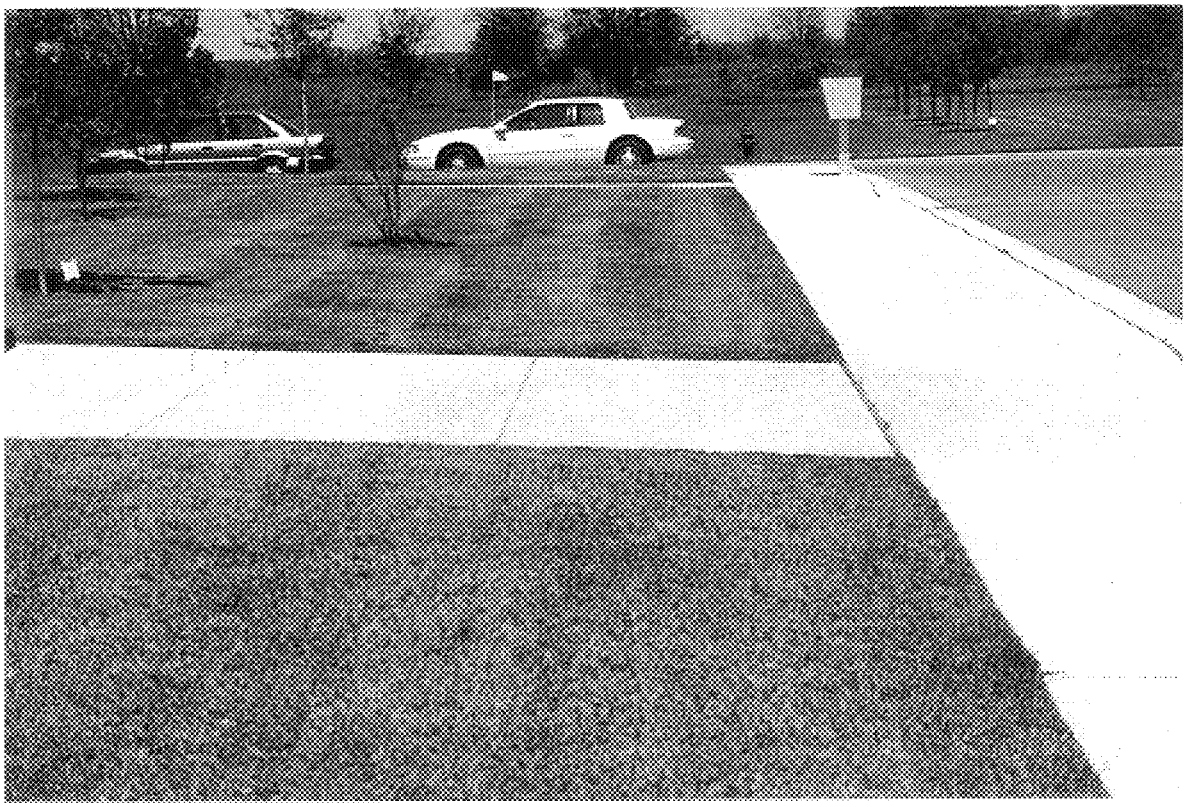
FIG. 1 is a photograph of 'JaMur' in the background and 'El Toro' in the foreground.
Figure 2:
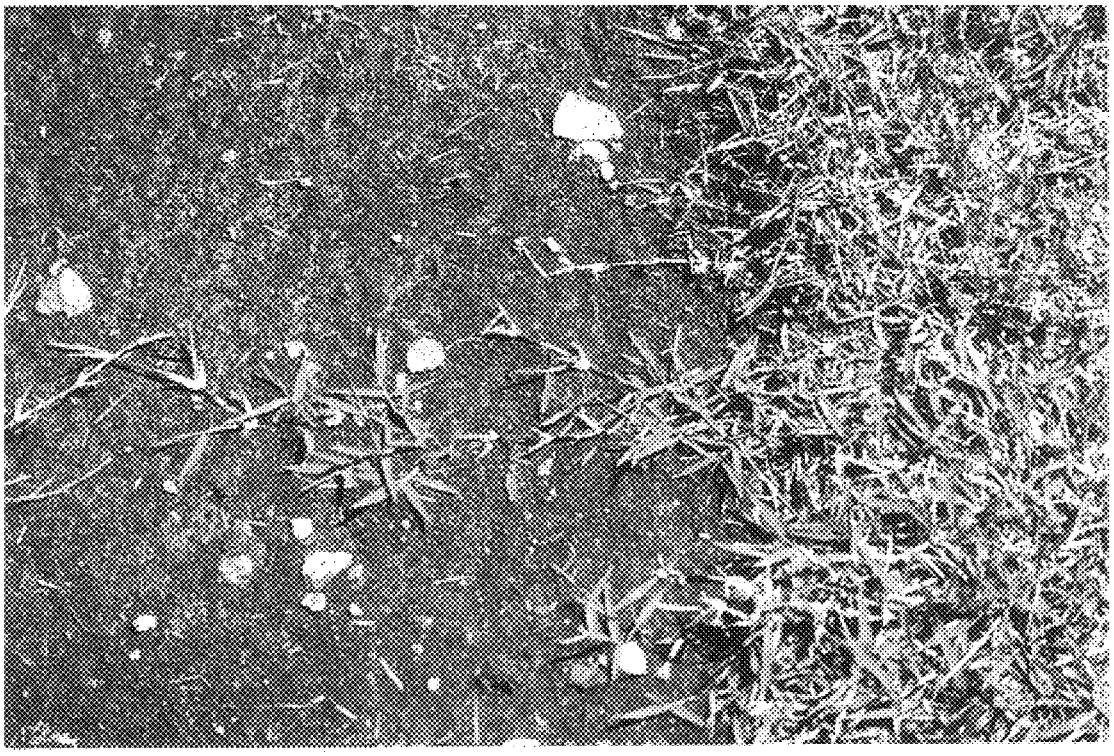
FIG. 2 is a photograph of a runner of 'JaMur'.
Figure 3:
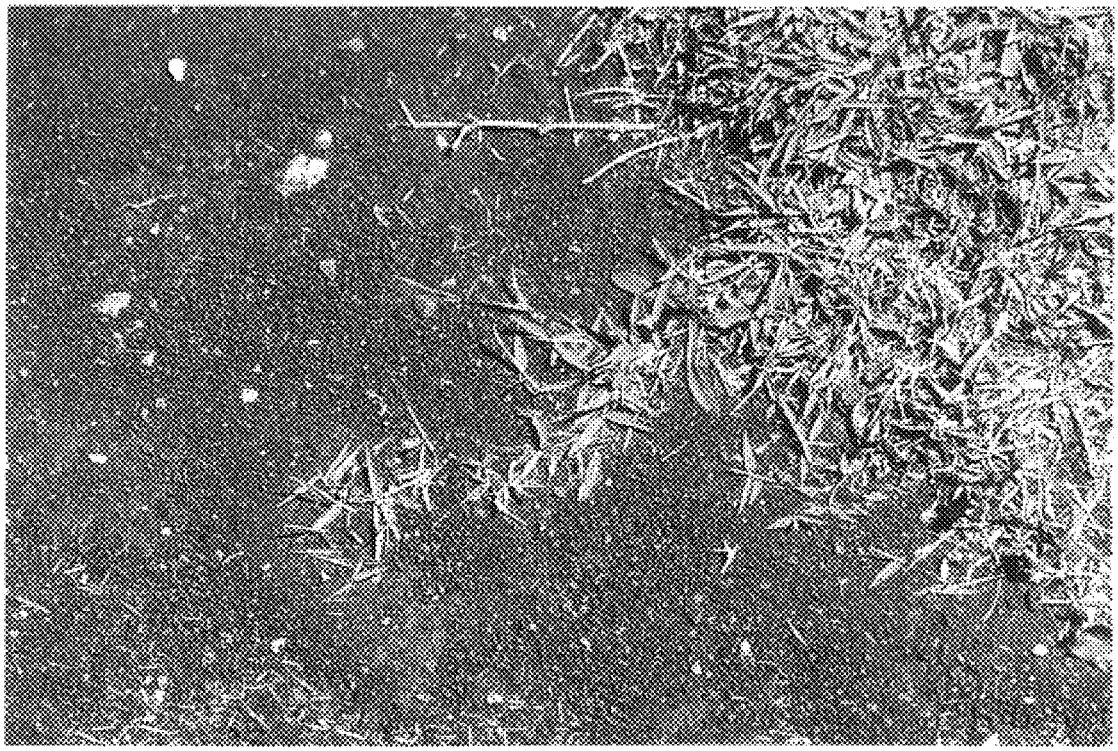
FIG. 3 is a photograph of a runner of 'El Toro'.
Figure 4:
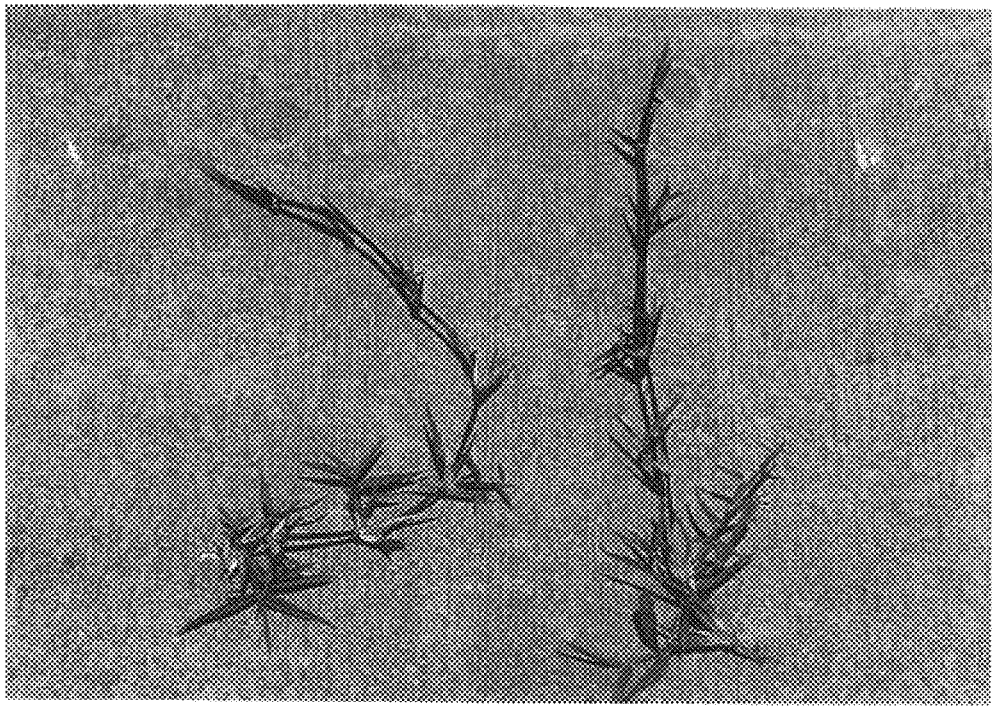
FIG. 4 is a photograph of the leaf orientation, blades and ligule of 'Omni' on the right and 'JaMur' on the left.
Figure 5:
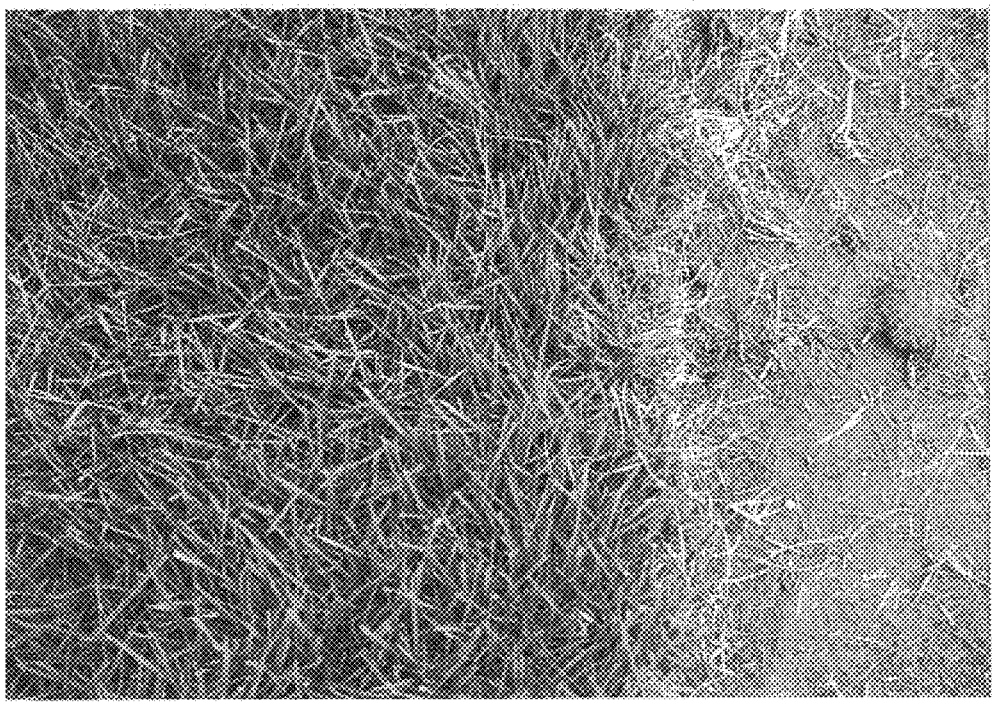
FIG. 5 is a photograph of 'Omni' solid sod.

'JaMur' was characterized in greenhouse and field conditions and is a unique variety of zoysia grass developed as described above. 'JaMur' has been propagated by stolon cuttings in Poteet, Tex. and all traits of the plant have been found to be stable through successive generations of asexual propagation.

The grass was planted in 1996 and grown in Carbondale, Ill. as part of the National Zoysiagrass Test conducted by the National Turfgrass Evaluation Program (NTEP). 'JaMur' had a superior rate of spreading and stolon frequency, comparable to that of 'El Toro' (U.S. Plant Pat. No. 5,845), and greater than all other standard varieties to which it was compared, as shown in Table 1.

TABLE 1

Traits of Selected Zoysiagrass Cultivars — Planted 1996, data 1997 and 2001, Carbondale, Illinois.

| | Stolon Length cm/m | Sod Spread cm | Stolon Freq. 9 = most | Texture 9 = finest |
|---|---|---|---|---|
| 'Chinese Common' | 127.1 | 2.7 | 7 | 2.0 |
| 'El Toro' | 311.6 | 4.9 | 9 | 4.3 |
| 'JaMur' | 426.5 | 4.7 | 9 | 5.7 |
| 'Meyer' | 48.6 | 2.2 | 5 | 7.3 |
| 'Emerald' | 91.2 | 1.3 | 5 | 8.3 |
| 'Zeon' | 372.0 | 1.2 | 5 | 9.0 |
| LSD 0.05 | 52.6 | 0.7 | | |

| | Thatch 9 = least | Posture 9 = vertical | Avg. Stolon Lgth cm |
|---|---|---|---|
| 'Chinese Common' | 2 | 6 | 14.66 |
| 'El Toro' | 4 | 8 | 17.38 |
| 'JaMur' | 9 | 4 | 17.42 |
| 'Meyer' | 3 | 9 | 5.55 |

TABLE 1-continued

Traits of Selected Zoysiagrass Cultivars — Planted 1996, data 1997 and 2001, Carbondale, Illinois.

| | | | |
|---|---|---|---|
| 'Emerald' | 1 | 7 | 6.56 |
| 'Zeon' | 8 | 8 | 11.60 |
| LSD 0.05 | | | 4.92 |

Also as shown in Table 1, 'JaMur' is described as having the least thickness of thatch and the texture of 'JaMur' was improved over that of 'Chinese Common' and 'El Toro', but not as fine as that of 'Meyer' (unpatented) or 'Emerald' (unpatented). Compared to the other grasses of Table 1, the posture of 'JaMur' was most prostrate.

Comparisons are shown in the tables that follow of internode length, thickness, and color, number of nodes from stolon tip to first branch, rate of branching per stolon node, stolon blade length and width, stolon sheath length, shoot blade length and width, shoot sheath length, and blade and ligule hair length and frequency. Using this information, 'JaMur' can easily be distinguished from 'Meyer', 'Emerald', 'Chinese Common' and 'El Toro'.

TABLE 2

Traits of Selected Zoysiagrass Cultivars — Planted 1996, data 1997 and 2001 Carbondale, Illinois.

| | Shoot Blade Length cm | Stolon Blade Length cm | Shoot Blade Width mm | Stolon Blade Width mm | Shoot Sheath Length cm | Stolon Sheath Length cm |
|---|---|---|---|---|---|---|
| 'Chinese Common' | 9.00 | 2.69 | 3.83 | 4.1 | 3.65 | 1.08 |
| 'El Toro' | 7.82 | 2.85 | 3.33 | 3.9 | 3.70 | 1.08 |
| 'JaMur' | 7.03 | 2.43 | 4.12 | 4.0 | 2.75 | 1.00 |
| 'Meyer' | 8.58 | 1.84 | 3.00 | 2.9 | 3.15 | 0.55 |
| 'Emerald' | 6.00 | 0.48 | 3.17 | 1.2 | 2.17 | 0.62 |
| 'Zeon' | 6.03 | 1.60 | 2.10 | 1.9 | 2.57 | 0.80 |
| LSD 0.05 | 0.94 | 0.31 | 0.50 | 0.4 | 0.49 | 0.16 |

As seen in Table 2, the shoot blade length of 'JaMur' was intermediate between that of 'Meyer' and 'Emerald', the same as that of 'El Toro', and shorter than that of 'Chinese Common'. Its stolon blade length was longer than that of 'Meyer' and 'Emerald' but shorter than that of 'Chinese Common' and 'El Toro'. The shoot blade width of 'JaMur' was greater than all other varieties. Its stolon blade width was the same as that of 'Chinese Common' and 'El Toro' but wider than of 'Meyer' and 'Emerald'. Shoot sheath length of 'JaMur' was shorter than that of 'Chinese Common' and 'El Toro' but the same as that of 'Meyer' and longer than that of 'Emerald'. Its stolon sheath length was the same as that of 'Chinese Common' and 'El Toro', but longer than that of 'Emerald' and 'Meyer'.

TABLE 3

Traits of Selected Zoysiagrass Cultivars — Planted 1996, data 1997 and 2001, Carbondale, Illinois.

| | Internode Length cm | Inter-node Width mm | Internode Color | Nodes to First Branch | Blade Hair Length mm | Ligule Hair Length mm |
|---|---|---|---|---|---|---|
| 'Chinese Common' | 4.65 | 2.00 | Dark Red | 4.00 | 2.8 | 2.00 |
| 'El Toro' | 4.13 | 1.00 | Dark Red | 1.67 | 1.2 | 2.17 |
| 'JaMur' | 4.78 | 1.95 | Dark Red | 2.00 | 1.0 | 1.95 |

TABLE 3-continued

Traits of Selected Zoysiagrass Cultivars — Planted 1996, data 1997 and 2001, Carbondale, Illinois.

| | Internode Length cm | Inter-node Width mm | Internode Color | Nodes to First Branch | Blade Hair Length mm | Ligule Hair Length mm |
|---|---|---|---|---|---|---|
| 'Meyer' | 1.82 | 1.88 | Red | 2.00 | 1.3 | 1.63 |
| 'Emerald' | 2.08 | 1.20 | Dark Red | 3.33 | 1.2 | 0.00 |
| 'Zeon' | 2.15 | 1.30 | Red | 1.50 | 1.0 | 2.50 |
| LSD 0.05 | 0.50 | 0.27 | | 0.61 | 0.3 | 0.30 |

As seen in Table 3, the stolon internodes of 'JaMur' were longest with those of 'Chinese Common', longer than those of 'El Toro', 'Emerald', and 'Meyer'. Internode thickness of 'JaMur' was the same as that of 'Chinese Common' and 'Meyer', but greater than that of 'Emerald' and 'El Toro'. Internodes of 'JaMur' were dark red, as were those of 'Chinese Common', 'El Toro', and 'Emerald', while the internodes of 'Meyer' and 'Zeon' were red. The number of nodes to the first branch from the stolon tip with 'JaMur' was the same as that of 'Meyer' and 'El Toro', but less than that of 'Emerald' and 'Chinese Common'.

Rate of branching in stolons was the same with all varieties, except that of 'Meyer', which was greater. The ligule hairs of 'JaMur' were the same length as those of 'Chinese Common', 'El Toro', and 'Meyer'. 'Emerald' had no ligule hairs. Ligule hairs of 'JaMur', 'El Toro', and 'Meyer' were frequent while those of 'Chinese Common' were dense. Blade hairs of 'JaMur' were the same length and space as those of 'El Toro', and shorter than the frequent blade hairs of 'Chinese Common' and 'Meyer'.

Tables 4 and 5 provide additional comparative data.

TABLE 4

Traits of Selected Zoysiagrass Cultivars — Planted 1996, data 1997 and 2001, Carbondale, Illinois.

| | Blade Hair Density | Stolons per Meter | Leaf Surface with Rust | Hairs % | Perimeter Stolon Length cm | Branches per Node |
|---|---|---|---|---|---|---|
| 'Chinese Common' | 3.3 | 9.1 | 1.7 | 96 | 54.37 | 0.90 |
| 'El Toro' | 2.0 | 19.0 | 2.0 | 78 | 68.67 | 1.28 |
| 'JaMur' | 1.3 | 24.1 | 1.0 | 62 | 63.88 | 1.11 |
| 'Meyer' | 2.0 | 7.5 | 2.0 | 58 | 28.57 | 2.60 |
| 'Emerald' | 2.0 | 14.1 | 1.0 | 68 | 32.25 | 1.40 |
| 'Zeon' | 2.3 | 24.5 | 1.0 | 100 | 34.55 | 1.01 |
| LSD 0.05 | 0.7 | 5.5 | 0.9 | 29 | 9.44 | 1.04 |

TABLE 5

Qualities of Turf in the National Zoysiagrass Cultivar Evaluation Trial, Planted 1996, Data 1997, Carbondale Illinois
Ratings- 9 = Darkest, Finest, Greatest, or Best

| | Turf Quality | | | | | | |
|---|---|---|---|---|---|---|---|
| | Color | Spg Grnp | Txtr | Jvn Vgr | May | Jun | Jul |
| HT-210 | 8.7 | 1.0 | 9.0 | 4.3 | 9.0 | 9.0 | 9.0 |
| DALZ 9601 | 8.0 | 7.7 | 9.0 | 4.0 | 8.7 | 8.7 | 8.7 |
| Zeon | 8.0 | 4.0 | 9.0 | 3.0 | 8.0 | 8.0 | 8.0 |
| FR | 8.3 | 1.0 | 9.0 | 1.0 | 7.7 | 7.7 | 7.7 |

TABLE 5-continued

Qualities of Turf in the National Zoysiagrass Cultivar Evaluation Trial, Planted 1996, Data 1997, Carbondale Illinois
Ratings- 9 = Darkest, Finest, Greatest, or Best

| | | | | | | | |
|---|---|---|---|---|---|---|---|
| Emerald | 8.0 | 6.0 | 8.3 | 5.7 | 8.0 | 8.3 | 8.3 |
| DeAnza | 7.0 | 1.0 | 7.7 | 5.3 | 7.7 | 8.0 | 8.0 |
| Meyer | 8.7 | 9.0 | 7.3 | 7.7 | 7.7 | 8.0 | 8.3 |
| J-14 | 7.7 | 9.0 | 6.3 | 7.3 | 7.7 | 8.0 | 8.7 |
| Victoria | 8.3 | 2.3 | 7.0 | 5.3 | 6.7 | 7.0 | 7.0 |
| OH-1 | 7.0 | 3.7 | 9.0 | 3.7 | 5.3 | 6.0 | 6.0 |
| JaMur | 6.3 | 1.7 | 5.7 | 3.7 | 6.0 | 7.3 | 8.0 |
| 2040 | 8.3 | 1.0 | 5.7 | 1.0 | 6.0 | 6.0 | 6.0 |
| El Toro | 5.3 | 2.3 | 4.3 | 7.7 | 6.0 | 7.0 | 7.7 |
| J-37 | 7.7 | 8.3 | 5.0 | 8.3 | 5.3 | 6.0 | 6.0 |
| Zenith | 7.7 | 8.3 | 6.0 | 6.0 | 5.0 | 5.3 | 5.0 |
| Miyako | 6.7 | 1.3 | 4.0 | 8.3 | 4.3 | 5.0 | 5.7 |
| SS | 7.3 | 1.0 | 5.3 | 1.0 | 4.3 | 5.0 | 5.0 |
| ZEN-400 | 5.7 | 9.0 | 4.3 | 4.3 | 5.0 | 5.0 | 5.3 |
| J-36 | 6.7 | 9.0 | 3.0 | 8.7 | 3.0 | 3.7 | 3.3 |
| ZEN-500 | 6.0 | 8.0 | 3.3 | 3.0 | 3.3 | 3.3 | 3.3 |
| Chinese Common | 4.7 | 9.0 | 2.0 | 7.0 | 3.0 | 3.3 | 3.7 |
| Korean Common | 4.7 | 1.0 | 1.0 | 1.0 | 3.3 | 3.7 | 4.3 |
| LSD 0.5 | 0.8 | 1.1 | 1.1 | 0.7 | 1.3 | 1.1 | 1.2 |

| | Turf Quality | | | | | |
|---|---|---|---|---|---|---|
| | Aug | Sep | Oct | Avg | % Sum Cover | % WtrKl |
| HT-210 | 9.0 | 9.0 | 9.0 | 9.0 | 1.0 | 1.0 |
| DALZ 9601 | 9.0 | 9.0 | 9.0 | 8.83 | 2.0 | 3.3 |
| Zeon | 8.7 | 9.0 | 9.0 | 8.44 | 1.7 | 2.0 |
| FR | 8.3 | 9.0 | 9.0 | 8.22 | 1.0 | 1.0 |
| Emerald | 8.3 | 8.0 | 8.0 | 8.17 | 2.3 | 4.7 |
| DeAnza | 8.3 | 8.0 | 8.0 | 8.00 | 1.3 | 1.0 |
| Meyer | 8.3 | 7.3 | 7.3 | 7.83 | 3.0 | 8.7 |
| J-14 | 8.0 | 7.0 | 7.0 | 7.72 | 3.7 | 8.7 |
| Victoria | 7.0 | 6.7 | 6.7 | 6.83 | 1.0 | 1.7 |
| OH-1 | 6.7 | 8.0 | 9.0 | 6.83 | 1.0 | 1.3 |
| JaMur | 7.0 | 5.7 | 5.0 | 6.50 | 1.0 | 1.7 |
| 2040 | 6.7 | 7.0 | 7.0 | 6.44 | 1.0 | 1.0 |
| El Toro | 6.3 | 5.3 | 5.0 | 6.22 | 4.0 | 2.0 |
| J-37 | 6.3 | 6.0 | 6.3 | 6.00 | 6.0 | 9.0 |
| Zenith | 6.0 | 6.7 | 7.0 | 5.83 | 5.0 | 8.3 |
| Miyako | 5.3 | 5.3 | 5.0 | 5.11 | 2.3 | 1.3 |
| SS | 5.0 | 5.0 | 5.0 | 4.89 | 1.0 | 1.0 |
| ZEN-400 | 5.0 | 4.3 | 4.3 | 4.83 | 6.3 | 8.7 |
| J-36 | 3.7 | 4.3 | 4.0 | 3.67 | 4.3 | 8.3 |
| ZEN-500 | 3.0 | 3.3 | 3.7 | 3.33 | 3.0 | 5.3 |
| Chinese Common | 3.3 | 3.0 | 2.7 | 3.17 | 6.7 | 9.0 |
| Korean Common | 3.3 | 2.0 | 1.7 | 3.06 | 5.0 | 1.0 |
| LSD 0.5 | 1.2 | 1.3 | 1.5 | 0.94 | 0.9 | 0.8 |

WtrKl = Winter Kill
Spg Grnp = Spring Greenup
Sum = Summer
Jvn Vgr = Juvenile Vigor

VARIETY

Origin: Cultivar of a single superior progeny of a superior vegetative plant selected from collection of plants from Kobe, Japan.

Classification: Botanic — *Zoysia japonica* Steud.

Chromosome number: n=20 (Diploid).

Form: *Monocot gramineae.*

Growth habit: A perennial plant with a stoloniferous growth habit that also produces rhizomes. This allows vegetative commercial propagation. It is able to spread under competitive conditions favorable for stolon production. It has a fibrous root system which can have a depth of 1 to 75 cm. It will produce a dense, intermediate-textured turf with medium dark green color throughout a growing season with temperatures ranging from around 45 F. to over 105 F.

Establishment rate:

*Plugs.*—8–24 weeks with irrigation.

*Sod.*—1–2 weeks.

*Sprigs.*—>one year.

Regions of adaptation: North/South from Northern Arkansas to Mexico, and East/West between both USA coasts. The full extent of the geographical adaptation of 'JaMur' may be greater and will only be limited by winter survival in colder regions and adequate precipitation in drier regions.

Blade: The leaf blade shape is a combination of lanceolate/ensiform. The leaf blades widen quickly from the collar to their greatest breadth, within a length of on centimeter. They then taper to a fine point at the tip. The blades are smooth and flat or gently smooth involute-capillary. There are no distinct differences in this morphology among the cultivars, except to the degree of width and length.

*Length.*—7 cm.

*Width.*—4 mm.

*Pubescence.*—Sparse across full adaxial surface.

Mature plant height: 10–20 cm.

Above canopy stolon production: None.

Internode length: 4.8 cm.

Internode width: 1.9 mm.

Stolon color: Dark red.

Leaf color: The leaf color is medium dark green. More specifically, the adaxial leaf surface, based on The R.H.S. Color Chart, is 137 C green group and the Abaxial leaf surface is 143 A green group.

Soil adaptation: Most soils with adequate drainage from sand to heavy clay loams and acid to alkaline pH.

Colors: Based on R.H.S. Color Chart, the anthers are 155 B white group, the stigmas are 157 A green-white group, the culms are 137 D green group and the blade hairs are 146 A.

What is claimed is:

1. A new zoysiagrass plant, substantially as herein described and illustrated.

* * * * *